United States Patent [19]

Takahashi

[11] Patent Number: 5,140,273

[45] Date of Patent: Aug. 18, 1992

[54] ELECTRODE SYSTEM TO FACILITATE DIELECTRIC MEASUREMENT OF MATERIALS

[75] Inventor: Hideyuki Takahashi, Tokyo, Japan

[73] Assignee: Hewlett-Packard Company, Palo Alto, Calif.

[21] Appl. No.: 504,680

[22] Filed: Apr. 4, 1990

[30] Foreign Application Priority Data

May 2, 1989 [JP] Japan .................................. 1-112906

[51] Int. Cl.$^5$ ........................................... G01R 27/26
[52] U.S. Cl. .................................... 324/671; 324/661; 324/663; 324/686; 324/688; 324/690
[58] Field of Search ............... 324/661, 662, 663, 664, 324/671, 686, 688, 689, 690

[56] References Cited

U.S. PATENT DOCUMENTS

| | | | |
|---|---|---|---|
| 4,294,321 | 10/1981 | Wittlinger et al. | 324/662 X |
| 4,568,873 | 2/1986 | Oyanagi et al. | 324/662 |
| 4,658,254 | 4/1987 | Walton | 324/662 |
| 4,855,667 | 8/1989 | Hendrick et al. | 324/670 |
| 4,881,025 | 11/1989 | Gregory | 324/671 X |
| 4,899,102 | 2/1990 | Hendrick et al. | 324/663 |
| 5,065,106 | 11/1991 | Hendrick et al. | 324/663 |

*Primary Examiner*—Kenneth A. Wieder
*Assistant Examiner*—Glenn W. Brown

[57] ABSTRACT

An electrode system (ES) according to the present invention provides greater flexibility in choosing the shape of the sample to be investigated, and reliable measurements when oriented in either a horizontal or vertical position. Moreover, means are provided for easily maintaining and calibrating the parallelism of the electrodes.

16 Claims, 10 Drawing Sheets

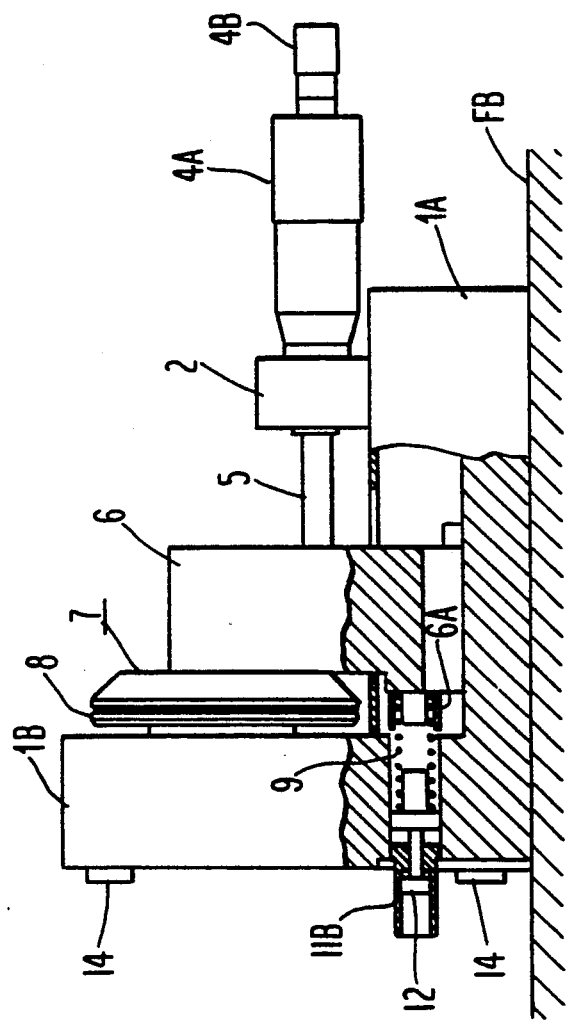
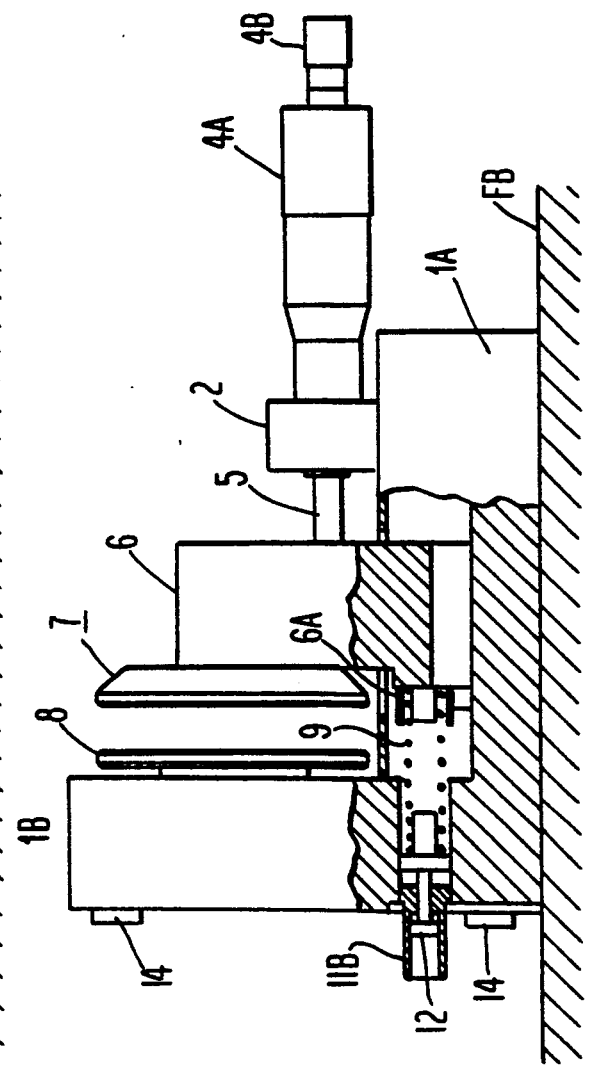

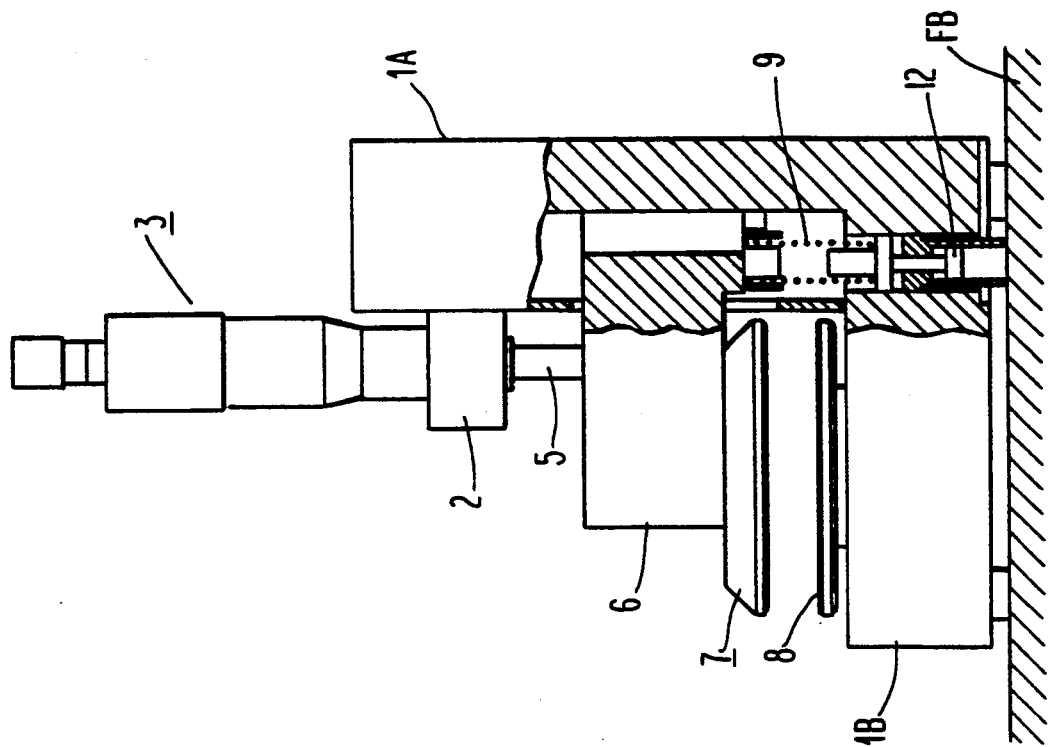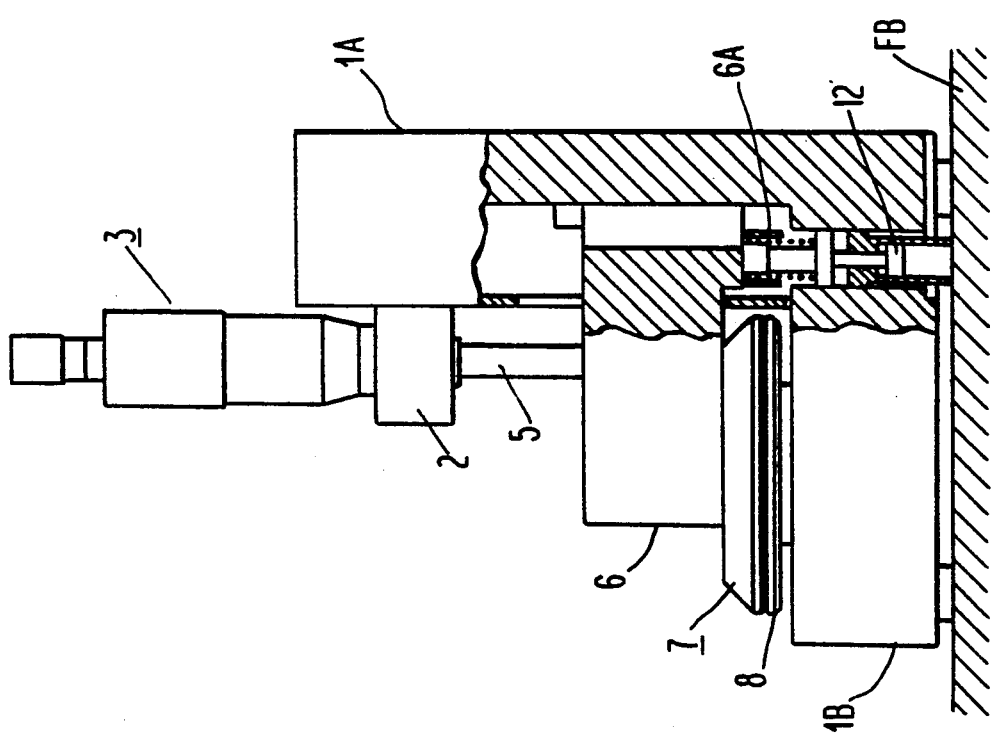

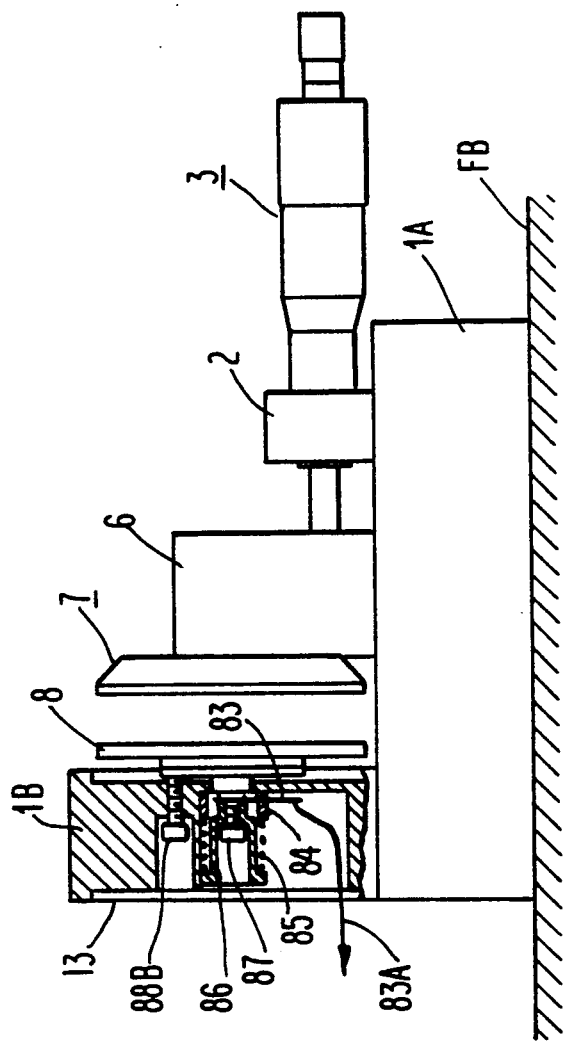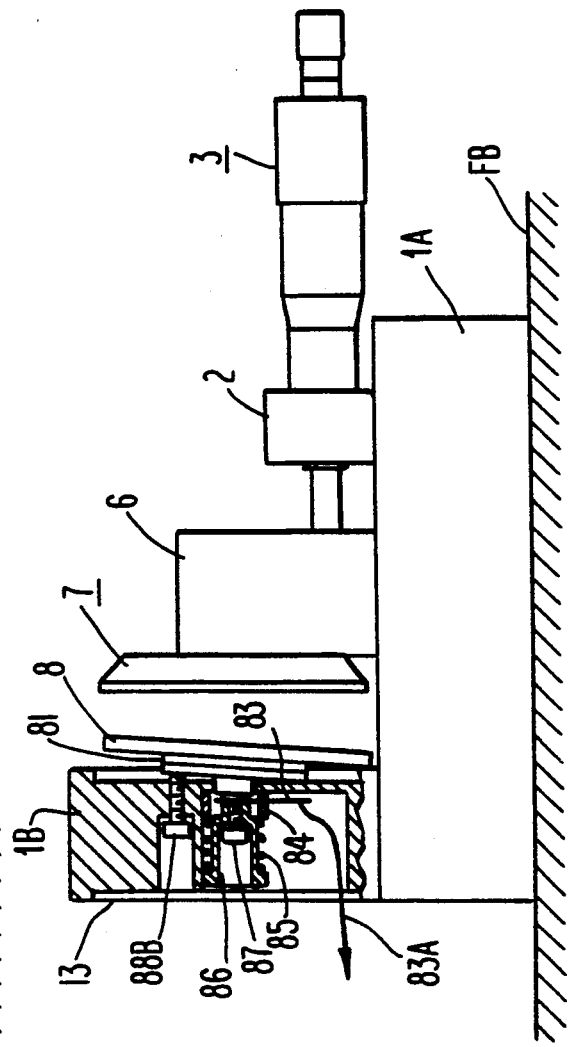
Fig. 5(A)
Fig. 5(B)

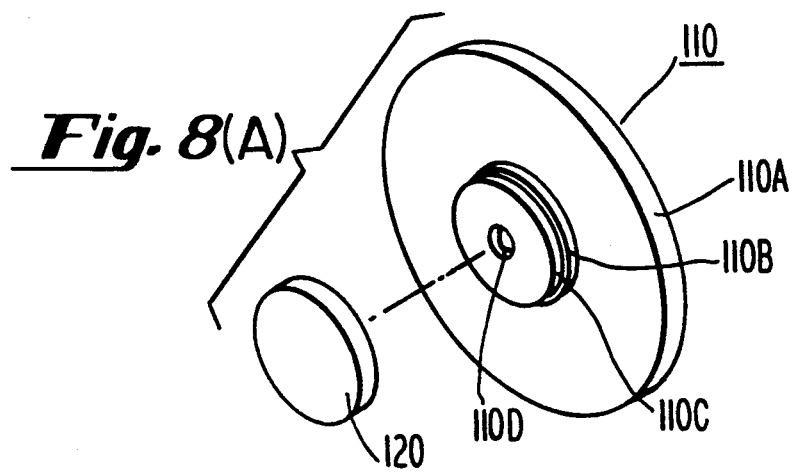
*Fig. 8*(A)
*Fig. 8*(B)
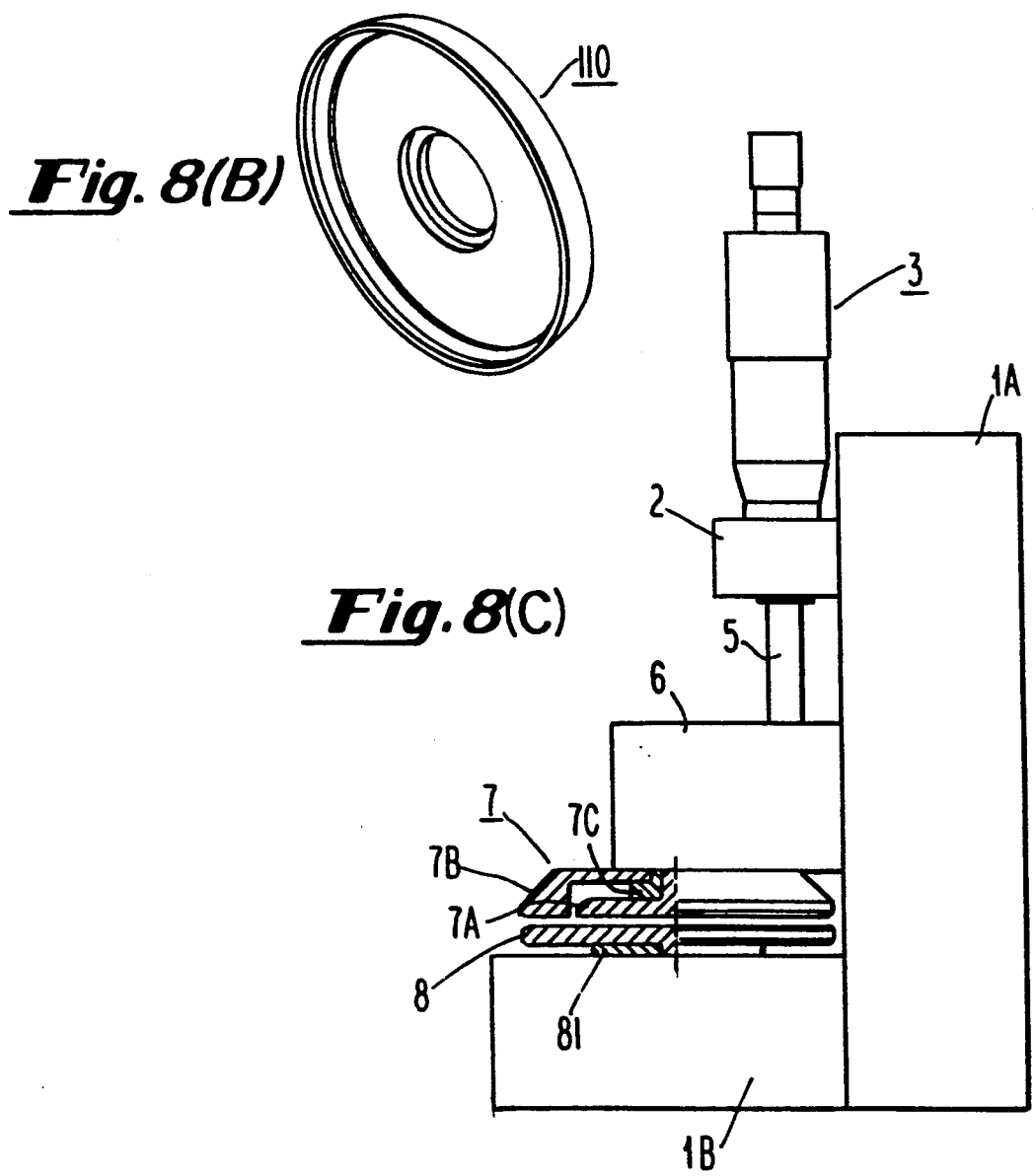
*Fig. 8*(C)

ELECTRODE SYSTEM TO FACILITATE DIELECTRIC MEASUREMENT OF MATERIALS

FIELD OF THE INVENTION

The invention is related to electrode systems for measuring electrical parameters of materials.

BACKGROUND OF THE INVENTION

Methods and apparatus for measuring an electrical parameter (dielectric constant, capacitance, dissipation factor etc.) of a material are described in the following publications, which are incorporated by reference herein: "ASTM D150-81: Standard Test Methods for A-C LOSS CHARACTERISTICS AND PERMITTIVITY (DIELECTRIC CONSTANT) OF SOLID ELECTRICAL INSULATING MATERIALS"; Hewlett Packard Application Note 339-13, "MEASURING THE DIELECTRIC CONSTANT OF SOLID MATERIALS:--HP 4194A Impedance/Gain--Phase Analyzer"; and Gen Rad Impedance Measurement APPLICATION NOTE 11, "Dielectric Loss and Permittivity Measurements with Gen Rad Precision Capacitance Bridges."

In prior art electrode systems (ESs), a material whose dielectric constant, for example, is to be measured is typically required to be in the form of a flat disk or plate having parallel surfaces. The ES therefore assumes the form of a parallel plate capacitor; that is, the ES comprises two planar electrodes which must be nearly perfectly parallel to one another. These limitations on the shape of the sample and on the shape and orientation of the electrodes present several practical problems, including maintaining the parallelism of the electrodes during normal use and after replacement of the electrodes, and accurately calibrating the measurement system. Moreover, prior art ESs are generally limited to either horizontal or vertical use, but not both. This later limitation is due to the fact that the pressure exerted on the sample being investigated significantly affects the measurements. Thus, prior art ESs designed for horizontal use cannot make accurate measurements when oriented vertically, and vice versa.

Accordingly, it is an object of the present invention to provide an ES which is convenient to use, comprises means for adjusting the parallelism of its electrodes, and can make accurate and reliable measurements in either a horizontal or vertical position. The present invention achieves these objectives.

SUMMARY OF THE INVENTION

The present invention provides an ES for horizontally or vertically measuring an electrical parameter of a sample. The ES comprises: (a) a frame; (b) a first electrode coupled to the frame; (c) a slider movably coupled to the frame; and (d) a second electrode coupled to the slider and substantially parallel to the first electrode. A preferred embodiment of the invention further comprises (e) force means disposed between the slider and frame for providing a force, the amount of which is adjustable depending upon whether the ES is horizontally or vertically oriented (or oriented at an angle between horizontal and vertical). According to the invention, the sample to be investigated is disposed between the first and second electrodes.

In another preferred embodiment, an ES according to the present invention further comprises micrometer means coupled to the frame and slider, for moving the slider, and the force means comprises a spring. Also, the first electrode is coupled to the frame with at least three set screws and a second spring. The set screws are engaged with the frame and disposed to push the first electrode away from the frame, and the second spring is disposed to pull the first electrode to the frame; thereby providing means for adjusting the parallelism of the electrode.

In one embodiment of the invention, the second electrode comprises a main electrode and a guard electrode insulated from the main electrode.

BRIEF DESCRIPTION OF THE DRAWINGS

FIGS. 2 (A and B) and 3 (A and B) are side elevation views partially in cross section of the ES shown in FIG. 1.

FIGS. 5 (A and B) are a side elevation view of the ES, for illustrating the operation of the adjusting mechanism shown in FIG. 4.

FIG. 8 and FIGS. 9 (A through views showing a jig for shorting and opening the ES, as well as the structure of the jig.

DETAILED DESCRIPTION OF PREFERRED EMBODIMENTS

The preferred embodiments will now be described with reference to the drawings, wherein like numerals designate like elements.

Figure 1:
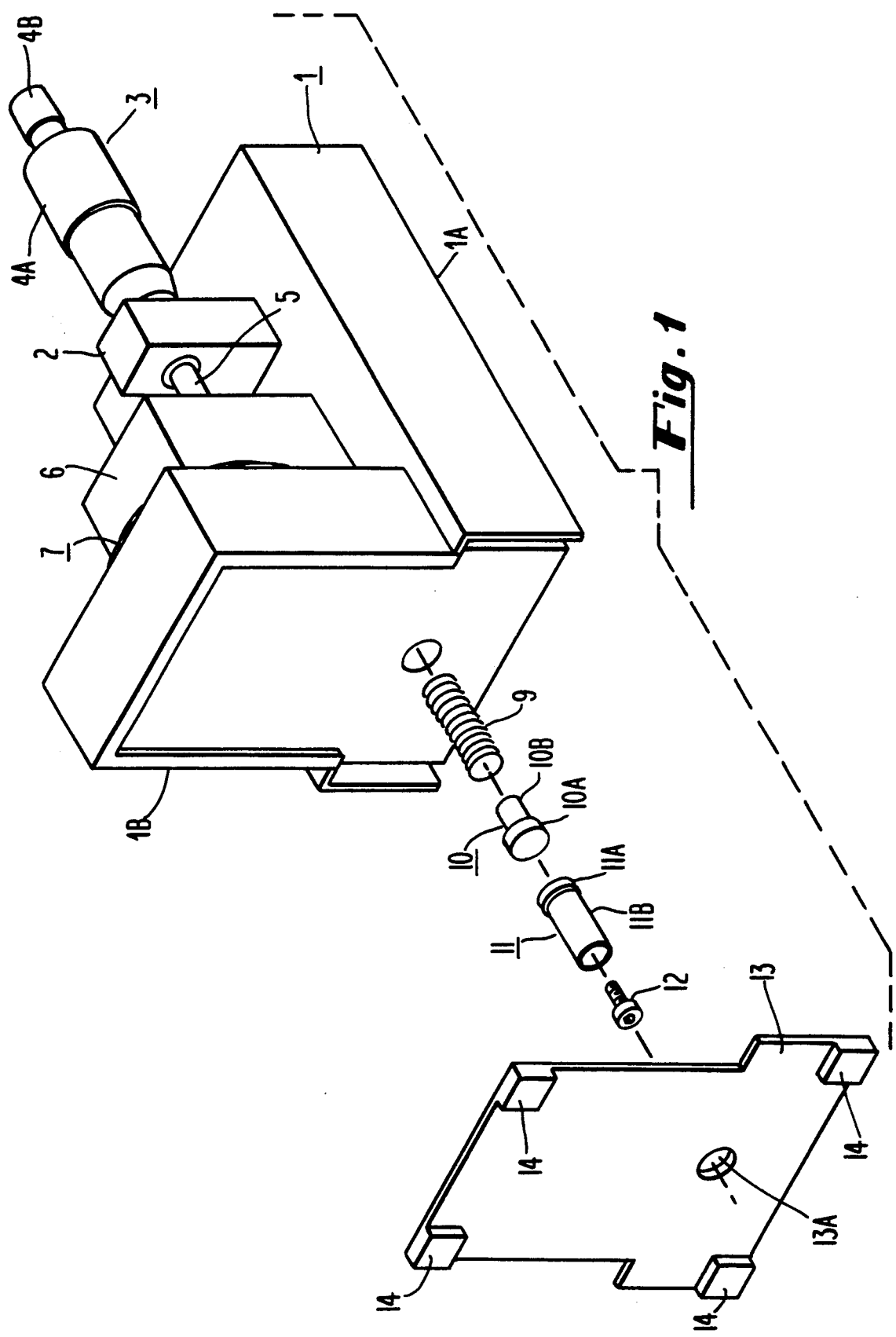
FIG. 1 is a partially exploded perspective view of an ES according to the invention.

Referring to FIG. 1, an ES according to the invention comprises an L-shaped frame 1 consisting of two blocks 1A, 1B at right angles to each other. In FIG. 1, the ES is oriented for horizontal measurement, i.e., the bottom surface of block 1A is in contact with a frame bed FB (see FIG. 2).

The first electrode 8 (see FIGS. 2, 3) is a "high", or "H", electrode, and is fixed by an adjusting mechanism described below.

The second electrode 7 is a "low", or "L", electrode, and is coupled to a slider 6 movably held on a rail (not shown) mounted on block 1A. Electrode 7 moves only horizontally. A preferred movable support mechanism is the BSP-1530 manufactured by the IKO Company of Japan. A sample to be investigated is sandwiched between the H electrode 8 and L electrode 7. A micrometer head 3 (for example the MHN$_3$-25 manufactured by Mitsutoyo Co., Ltd. of Japan) is mounted on a mount 2 that is fixed to frame 1. The micrometer has a spindle 5 which is moved back and forth by a thimble 4A and a ratchet stop 4B. A measured surface perpendicular to the axis of the spindle bears on the opposite side of the mounting surface of L electrode 7 of slider 6, the opposite side being substantially parallel to the measured surface. Slider 6 is pushed horizontally. The horizontal force acting on slider 6 towards spindle 5 is applied by spring retainer 6A (FIGS. 1 and 2), spring 9, spring retainer 10, holder 11, spring force-adjusting screw 12, and cover 13. Spring retainer 6A extends through a guide hole in block 1B of the frame. Each of these components is formed so as to exhibit rotational symmetry with respect to an axis which is common to all of them. The components are disposed parallel to the axis of spindle 5.

The stopper for holder 11 and the guide hole can be designed not to exhibit rotational symmetry. In this case, an adjustment using spring force-adjusting screw 12 can be made with greater ease.

FIGS. 2(A) and 2(B) are cross sections taken through the central axes of holder 11, spring retainer 6A, etc., for showing the manner in which a spring force is applied to slider 6.

Spring retainer 6A is a hollow cylinder fixed to slider 6. The right end of spring 9 is received in the cylinder. The body 10B of spring retainer 10 is a solid cylinder and inserted a given distance into the left portion of spring 9. Spring retainer 10 comprises flange 10A the diameter of which is set larger than the inside diameter of spring 9 to restrict the left end of spring 9. Therefore, the total length of spring 9, and hence the spring force, is determined by the distance between the right side surface of flange 10A and the left side surface of slider 6.

Holder 11 has a force rod 11B the diameter of which is smaller than the inside diameter of adjusting hole 13A. Holder 11 further includes a stopper 11A the diameter of which is set larger than the inside diameter of adjusting hole 13A. A spring force-adjusting screw 12 is inserted into a hole formed in force rod 11B of holder 11 and screwed into a tapped hole formed at the bottom of the hole in rod 11B. Screw 12 extends to the right from holder 11 and bears on the central portion of the left side surface of flange 10A.

The force of spring 9 which acts to the left limits the position of holder 11 such that the right side surface of cover 13 bears on the left side surface of the stopper 11A of holder 11. The position of flange 10A is shifted by adjusting the amount of protrusion of screw 12, to vary the total length of the spring 9. As a result, the force applied to slider 6 which is mounted on frame 1 is varied.

FIG. 2(A) depicts the condition in which L electrode 7 is in contact with H electrode 8. FIG. 2(B) depicts the condition in which L electrode 7 is separated from H electrode 8.

FIGS. 3(A) and 3(B) show the ES of FIG. 2 oriented vertically rather than horizontally, as shown in FIGS. 2(A) and 2(B). In FIG. 3(A), L electrode 7 is in contact with the H electrode 8. In FIG. 3(B) L electrode 7 is separated from H electrode 8.

If force rod 11B is longer than the height of legs 14 and protrude to the left as shown in FIG. 2, then it (force rod 11B) will be pushed to the surface of frame bed FB, as shown in FIG. 3. In this case, the total length of spring 9 will be shortened, provided that the positional relation between slider 6 and frame 1 is not varied. In this way, the weight of slider 6 itself can be compensated for in the vertical usage. This reduces the difference in force applied to the measured sample between the horizontal usage and the vertical usage. This feature enables an ES according to the present invention to provide reliable measurements in both the horizontal and vertical configuration.

In the description made in connection with FIGS. 1–3, only those features which are needed to explain the operation of spring 9 are described below. The remaining features are not described, as they will be apparent to those skilled in the art.

The plates of H electrode 8 and L electrode 7 are perpendicular to the axis of spindle 5. It is convenient to pull a cable connected with an LCR meter, such as an HP4284, from the L-shaped bent portion of frame 1 perpendicularly to the plane of FIGS. 2 and 3. The LCR meter (not shown) can be arranged to conduct four terminal pair measurements. Frame 1, slider 6, and the outer periphery of L electrode 7 are electrically connected with each other to form a guard electrode. A measuring voltage is applied between H electrode 8 and the guard electrode for measurement. Preferably slider 6 will be connected with frame 1 by a flexible electrical wire. Electric current is drawn from the main electrode (i.e., the internal electrode) of L electrode 7. The potential difference between the guard electrode and the main electrode asymptotically approaches zero, and so the two electrodes are virtually shorted. The impedance of a sample sandwiched between L electrode 7 and H electrode 8 is obtained from the ratio of the voltage applied between H electrode 8 and the guard electrode to the current flowing through the main electrode. This is described in detail below.

A mechanism for adjusting the parallelism between L electrode 7 and H electrode 8 is described next with reference to FIGS. 4 and 5. The plates of the electrodes are planar. In the partially exploded perspective view of FIG. 4, the electrode system is oriented horizontally as in FIG. 1. Also, components mounted to H electrode 8 are shown.

Depending upon errors produced in assembly or contained in the materials, the parallelism between the contacting surfaces of both electrodes may not be sufficient to accurately measure a sample that has parallel surfaces. The parallelism of the electrodes often deteriorates particularly when the electrodes are replaced.

FIG. 5(A) depicts a vertical cross section through the centers of mounted components in which the parallelism between the electrodes is high. FIG. 5(B) depicts a cross section similar to FIG. 5(A), but in which the parallelism is low. The lower block 1B is provided with four guide holes into which the aforementioned components are inserted. These guide holes have cross sections shown in FIG. 5 The right ends of the guide holes are tapped, enabling H electrode-adjusting screws 88A–88C to engage therewith. FIG. 5 also shows a terminal 83A to which an LCR meter (not shown) can be coupled.

Figure 4:
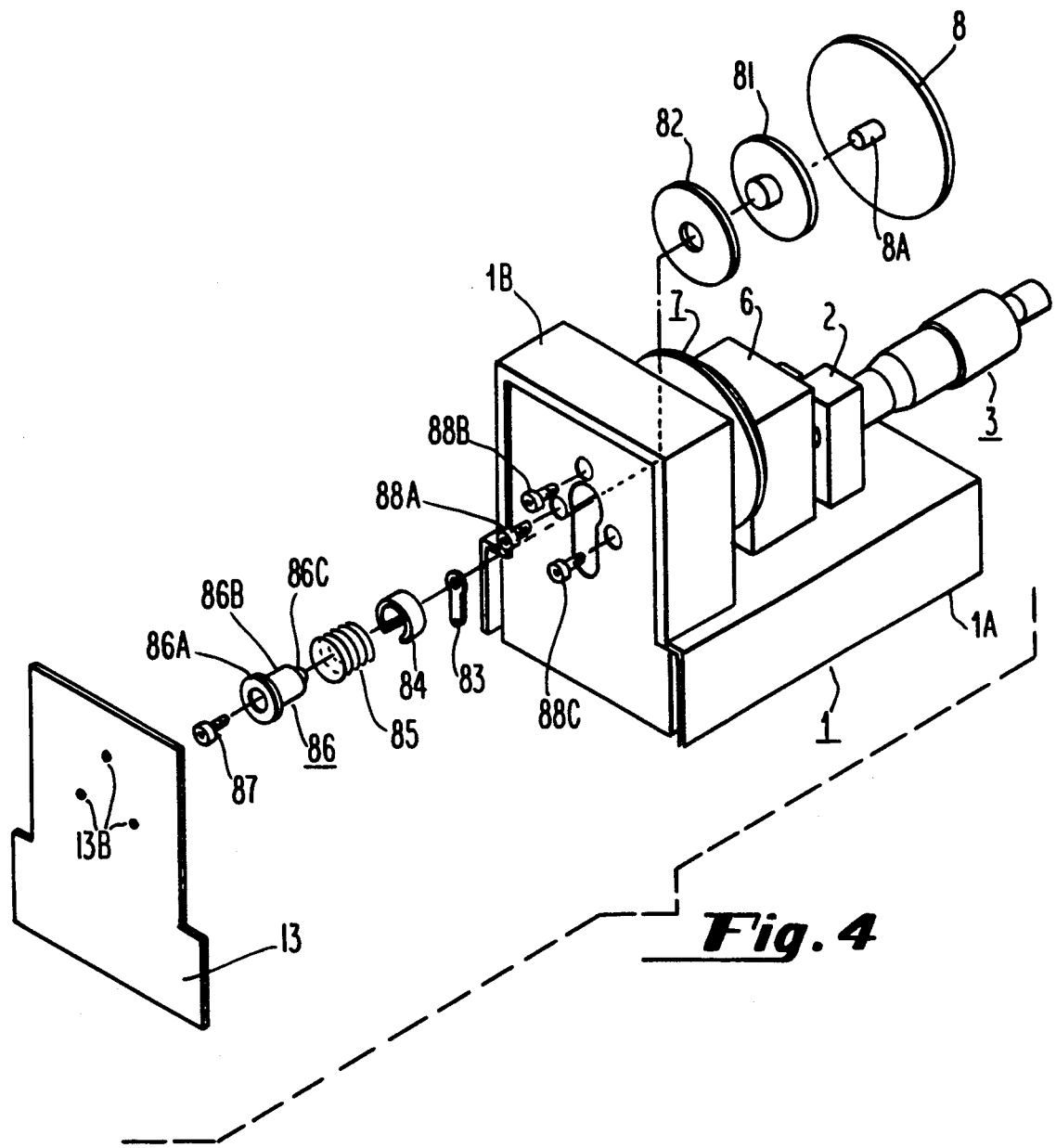
FIG. 4 is an exploded view of an electrode parallelism-adjusting mechanism according to the invention.

Referring now to FIGS. 4 and 5(A), H electrode 8, space 81 (preferably made from polyacetal resin) and screw retainer plate 82 (preferably made of steel) are simultaneously moved from the right side so that they bear against lower block 1B, by means of a tapped protrusion 8A formed in the center of H electrode 8. H electrode 8, female screw 87, spring holder 86 (made of an insulator), spring 85, spacer 84, and lug terminal 83 are sequentially inserted from the left side into an I-shaped guide formed in lower block 1B of the frame. Female screw 87 is brought into engagement with the central protrusion 8A of H electrode 8 to assemble them into a unit. Spacer 81 has a cylindrical protrusion 81A the outside diameter of which is smaller than the diameter of spacer 84 to permit spacer 84 to bear on the right side of the bottom of the I-shaped guide hole.

Spring holder 86 comprises flange 86A, body 86B, and neck 86C which are arranged as shown. Their outside diameters decrease in the order shown. Thus, female screw 87, spring holder 86, lug terminal 83, screw retainer 82, spacer 81, and H electrode 8 ar coupled together to form a unit. Spring 85 is disposed between flange 86A of spring holder 86 and spacer 84. The unit described above is biased to the left relative to frame 1B by the spring (i.e., away from the frame). A slight gap is left between the I-shaped guide hole and the unit to allow them to move relative to each other. The orientation of H electrode 8 is determined by the three screws 88A-88C adjusting the parallelism.

Lug terminal 83 acts to connect H electrode 8 with a lead wire of a measuring instrument (not shown) such as the LCR meter mentioned above. This terminal is insulated from frame 1.

Referring now to FIG. 5(B), the tilt of H electrode 8 is grossly exaggerated for illustration purposes. The parallelism is calibrated in the manner described next with reference to FIG. 6.

Figure 6:
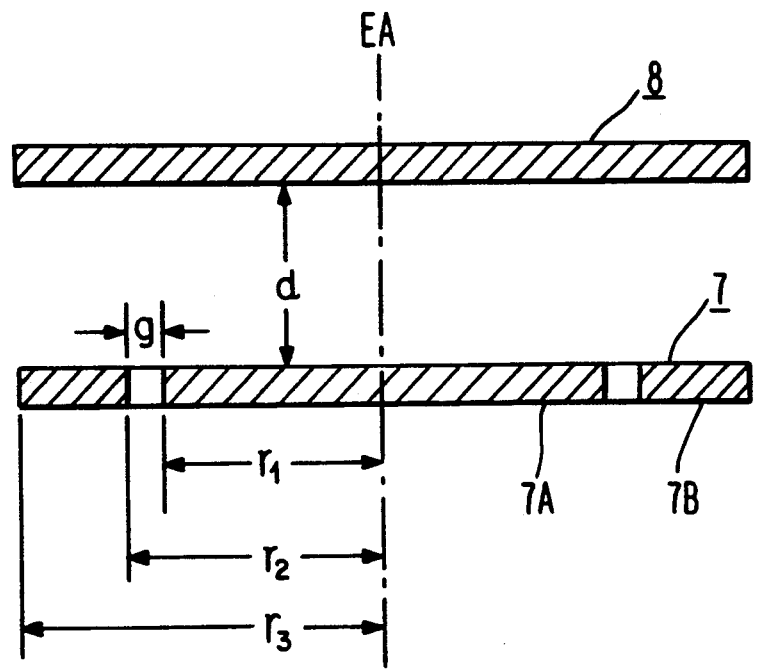
FIGS. 6 and 7 are views indicating the dimensions needed for calculating the capacitance of ES.

Referring now to FIG. 6, an electrode configuration for illustrating the calibration is shown wherein L electrode 7 and the H electrode 8 are so disposed that their contact surfaces face each other. These contact surfaces have an axis EA parallel to the central axis of spindle 5. L electrode 7 is composed of a main electrode 7A and an annular protective electrode 7B. Main electrode 7A has a radius of $r_1$, and protective electrode 7B has an inside radius of $r_2$ and an outside radius of $r_3$. The length of gap g is given by $g = r_2 - r_1$. The distance between the contact surfaces is designated by d. Preferably, outside diameter $r_3$ of protective electrode 7B is selected so that the value $r_3 - r_2$ is larger than the length of gap g by a factor of more than 10.

In one example of the invention, $r_1 = 0.0190(m)$, $r_2 = 0.0192(m)$, $g = r_2 - r_1 = 0.0002(m)$, $r_3 = 0.028(m)$, and $(r_3 - r_2)/g = 44$.

In another example of the invention, $r_1 = 0.0025$, $r_2 = 0.0027$, $g = 0.0002$, $r_3 = 0.010$, and $(r_3 - r_2)/g = 36.5$.

Figure 7:
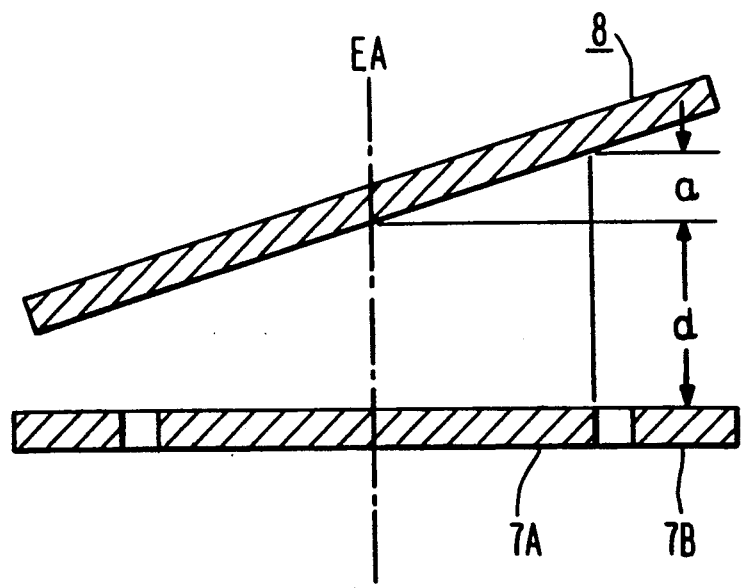
Figure 9A:
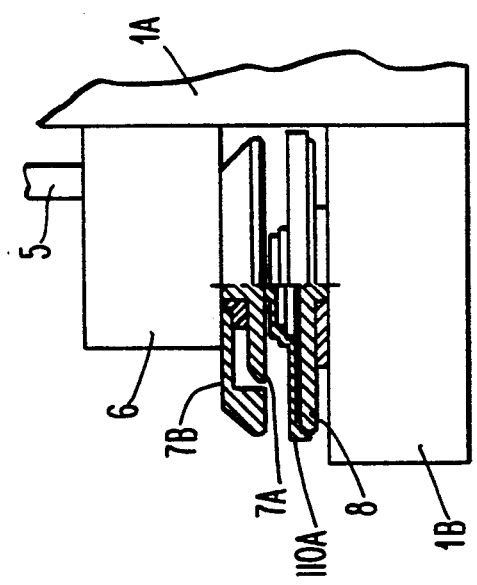
Figure 9B:
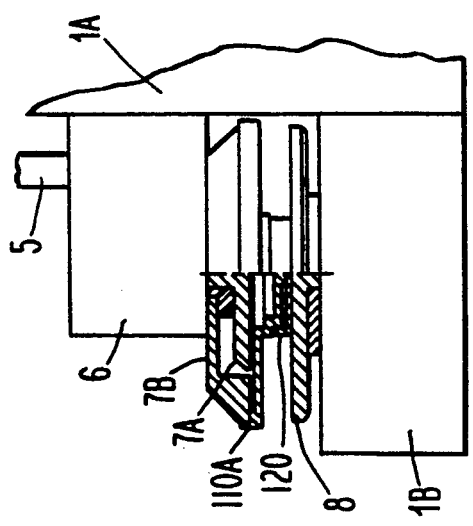
Figure 9C:
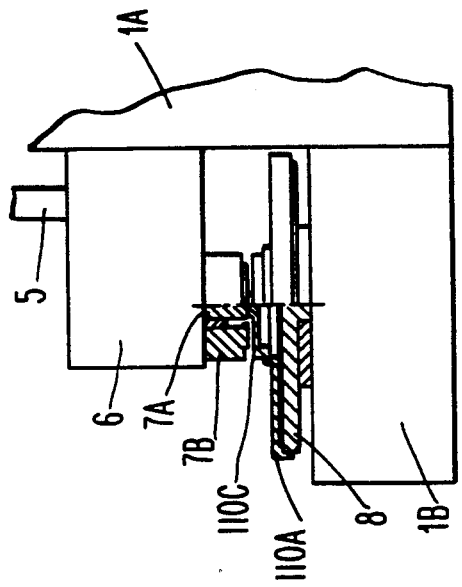
Figure 9D:
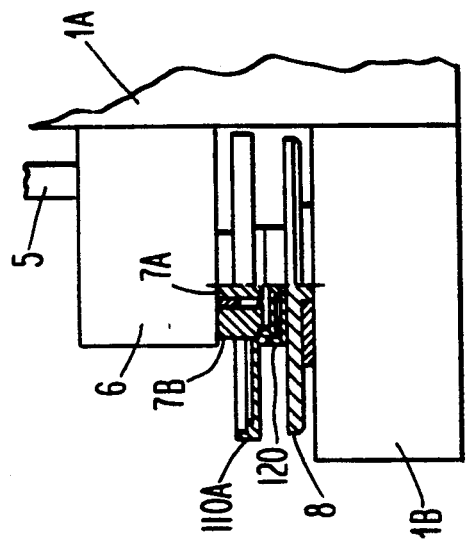

When H electrode 8 is inclined as shown in FIG. 7, the electrostatic capacitance C(a) of H electrode 8 and main electrode 7A is given by $$C(a) = \frac{\epsilon r_1^2}{d} \cdot \frac{2}{(a/d)^2} \cdot \{1 - \sqrt{1 - (a/d)^2}\} \quad (1)$$

The above equation indicates the condition in which H electrode 8 is inclined on the outer periphery of main electrode 7A by an amount a, provided that $a < d$. In the above equation, $\epsilon$ indicates the ambient dielectric constant. If the surroundings are air, $\epsilon = 1.0059 \times 8.8542 \times 10^{-12}$ F/m. Note that the relation $C(a) < C(0)$ generally holds.

The calibration procedure comprises the following steps:

1) An LCR meter is connected, with its operating mode set to measure capacitance. Then C(a) is measured.

2) The micrometer is operated to bring L electrode 7 as close as possible to H electrode 8.

3) The orientation of H electrode 8 is adjusted with the parallelism-adjusting screws 88A-88C while observing it visually so that the space between both electrodes is uniform.

4) The micrometer is operated to bring the electrodes into contact with each other. If a gap is seen between the electrodes, the parallelism adjusting screws 88A-88C are loosened to increase the distance between both electrodes while bringing them closer to each other with the ratchet stopper, thereby eliminating the gap.

5) The scale on the micrometer is set to the minimum value, e.g., in the present example 10 μm. A check is made of whether the capacitance C(a) lies in a tolerable range of the theoretical values given by equation (1). If the capacitance does not lie within this range, then the capacitance is varied with the parallelism adjusting screws 88A-88C. In one example of the invention, the parallelism is set to 10 μm. In the abovedescribed first example where $r_1 = 0.019$, $r_2 = 0.0192$, and $r_3 = 0.028$, the capacitance is adjusted to between 700 to 1000 pF.

The noncontacting calibration performed capacitively in this way is more advantageous than the contacting method because the effects of unevenness (e.g., 1 to 2 μm) of the electrode plates are minimized.

It is necessary to calibrate the measuring system including the LCR meter by shorting out and opening the ES. In one example of the invention, the ES is repeatedly shorted out and opened with high reproducibility by the use of the short-circuit jig 110 and a contact cover 120 shown in FIG. 8(A). Contact cover 120 is preferably made from polyacetal resin. One example of an electrode structure on which short-circuit jig 110 and contact cover 120 are mounted is shown in FIG. 8(C), where L electrode 7 comprises main electrode 7A and protective electrode 7B separated by an insulator 7C. H electrode 8 is shown in cross section through its mid point.

Referring now to FIG. 8(A), jig 110 comprises coaxial cylinders 110A-110C having coaxial disks. The cylinders are assembled in decreasing order of diameter. Coaxial cylinder 110C has a contact 110D that is a semispherical protrusion. The inside diameter of the contact cover 120 is equal to the outside diameter of coaxial cylinder 110C. The depth of cover 120 is equal to the sum of the height of coaxial cylinder 110C and the height of contact 110D. FIG. 8(B) is a rear view of short-circuit jig 110, and FIG. 8(A) is a front elevation view of jig 110.

The manner in which jig 110 and contact cover 120 are mounted is shown in FIG. 9. In FIGS. 9(A) and (B) L electrode 7 is large, while in FIGS. 9(C) and (D) L electrode 7 is small. FIGS. 9(A) and (C) show short-circuited conditions; FIGS. (B) and (D) show open conditions. As shown in FIG. 9, the inside diameter of coaxial cylinder 110A is set equal to the dimension of the large L electrode, and the inside diameter of coaxial cylinder 110B is set equal to the dimension of the small L electrode. In any of FIGS. 9(A)-(D), both electrodes are brought sufficiently close to each other to ensure mechanical stability and to permit measurements to be made reliably.

Figure 10A:
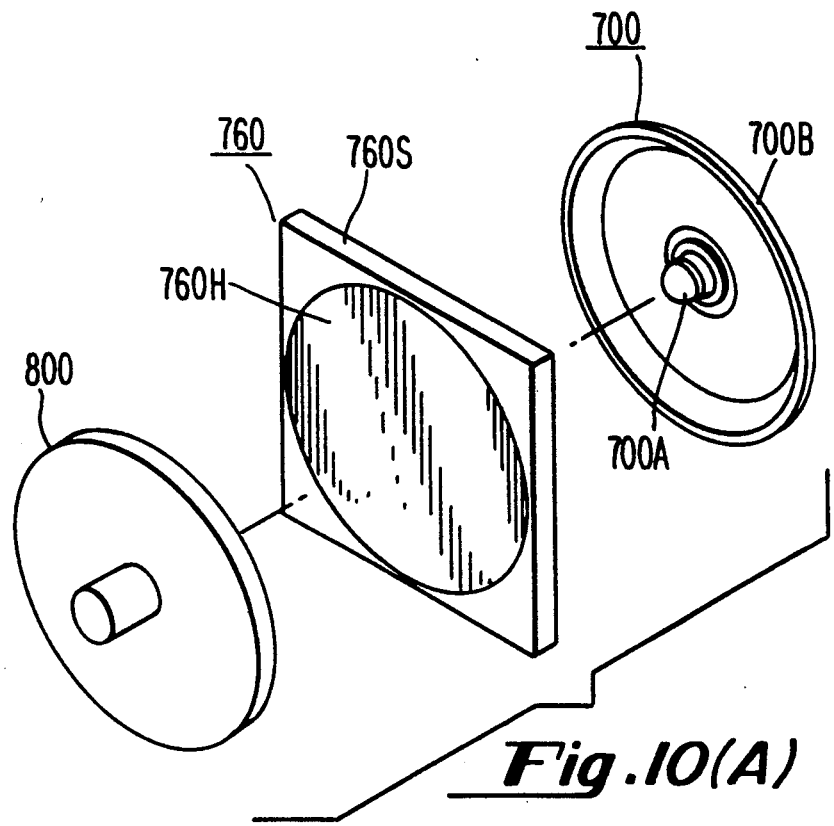
FIGS. 10 (A through B)
Figure 10B:
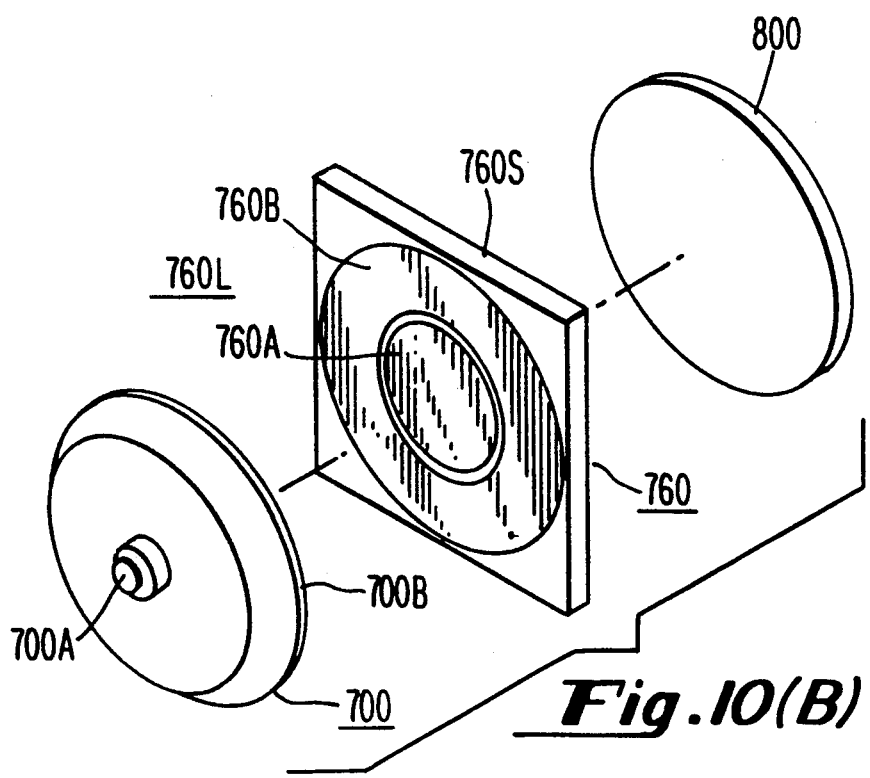

FIG. 10 depicts a special electrode structure for precisely measuring an electrical parameter of a sample 760S in the form of parallel plates. FIG. 10(A) is a perspective view showing the relation of the electrodes to the sample, as viewed from one direction. FIG. 10(B) is a view similar to FIG. 10(A), but viewed from the opposite direction. Preferably, H electrode 800 will be essentially the same as the above-described H electrode 8. Sample 760S is in the shape of a flat plate. For an accurate measurement, an electrode is directly deposited onto the sample under investigation. This deposition is accomplished by, for example, sticking on metal foil with a grease (for example, Vaseline TM petroleum jelly), applying a metal paste, printing metal onto the sample, or by some other suitable method.

The prior art electrode will preferably have a shape defined by a standard, such as, for example, the Japanese Industrial Standard. Typically, the measuring electrode will have the same shape as the deposited electrode.

Sample 760S has a H electrode 760H and an L electrode 760L, both of which are deposited. H electrode 760H is opposite to H electrode 800. L electrode 760L is opposite to L electrode 700, and comprises an electrode 760B protecting the sample together with a main electrode 760A. L electrode 700 includes a guard electrode 700B and a main electrode 700A.

Figure 11:
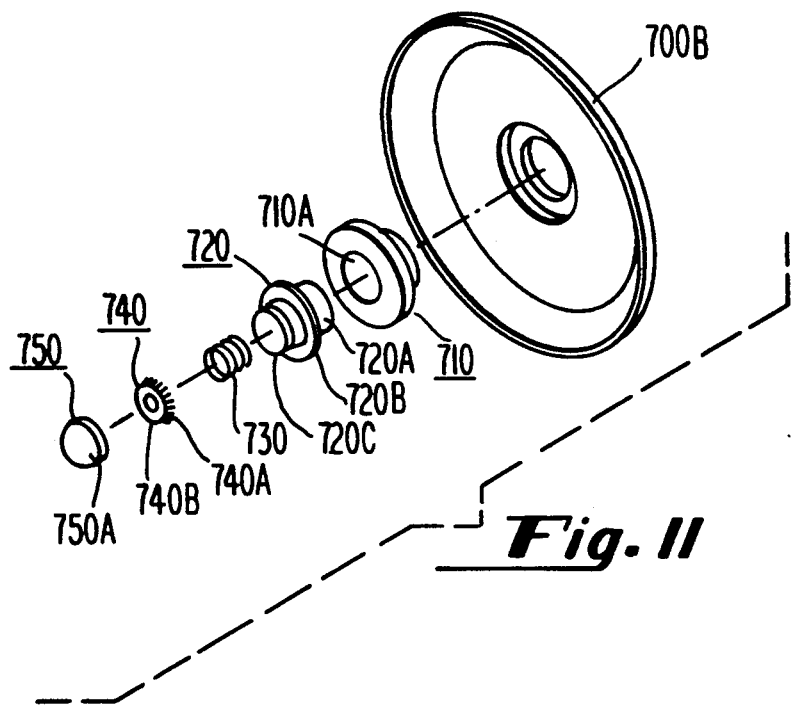
FIG. 11 and FIG. 12 are views showing an electrode for investigating a sample on which a thin film electrode is deposited.

Referring now to FIG. 11, therein is depicted an exploded view of L electrode 700 of FIG. 10. A recess is formed in the center of the platelike guard electrode 700B. An opening is formed in the center of the recess. An insulator 710 is fixed into the opening by press fit or a screw. Insulator 710 is provided with a hole 710A extending through it. The body 720A of an electrode-holding conductor 720 extends through hole 710A and is connected with a lead wire of a measuring instrument (not shown). The distance over which the body 720A is inserted is determined by a stopper 720B. A neck portion 720C has a blind hold in which a spring 730, a contact brush 740, and a contact portion 750 are partially inserted. Three retaining pins 740B are inserted in holes (not shown) formed in contact portion 750 to couple contact brush 740 to contact portion 750. A number of resilient elements 740A are in contact with the inner surface of the blind hole in the neck portion 720C to improve the contact between contact portion 750 and electrode-holding conductor 720.

Contact portion 750 has a semispherical contact 750A. After inserting a part of contact 750 into neck portion 720C, the end of neck portion 720C is narrowed to prevent the contact portion from coming off neck portion 720C.

Figure 12:
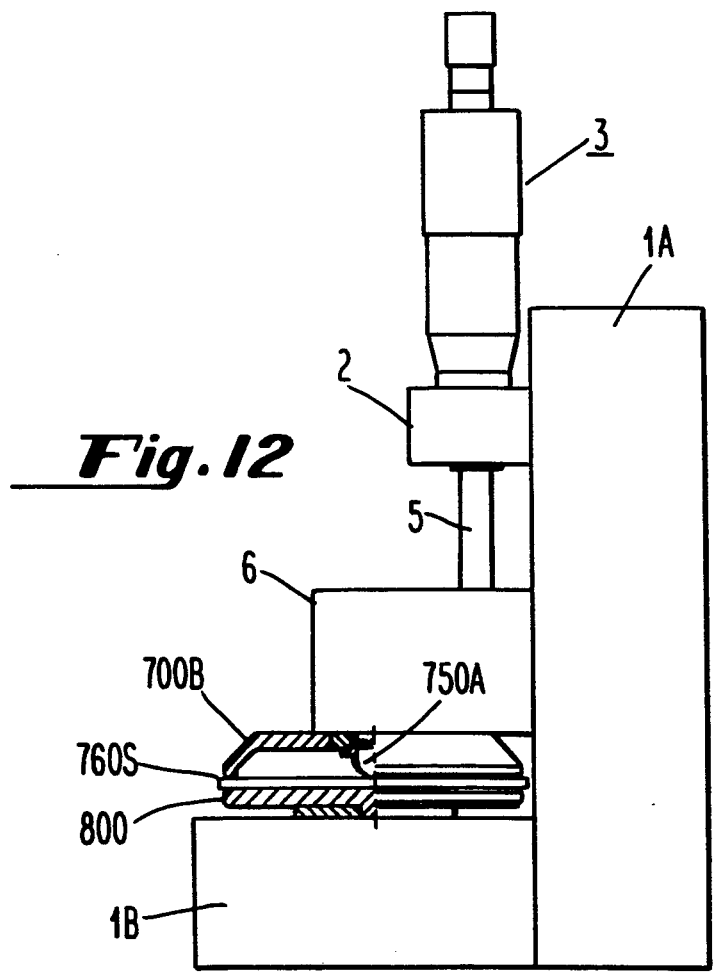

FIG. 12 shows the condition in which sample 760S is inserted in the same way as in FIG. 8(C). This configuration provides a greater degree of freedom to the shapes of main electrode 760A and sample protective electrode 760B. This enhances the ES's convenience of use.

The intrinsic impedance of the sample is given by $$Z = \frac{V}{i} \cdot \frac{S}{d} \qquad (2)$$

where S is the area of the deposited main electrode 760A, d is the thickness of sample 760S, V is the measured voltage applied to H electrode 800, and i is the electric current flowing through main electrode 760A of L electrode 700. The resistivity and the dielectric constant are obtained from the value of Z by known methods.

In summary, an ES according to the present invention provides means for maintaining good parallelism between the electrodes, and reliable measurements in both horizontal and vertical usage. When a sample is investigated by depositing on it a thin film electrode, a greater degree of freedom is available for selecting the sample shape. This is very convenient for practical purposes.

Although preferred embodiments have been described herein, many variations thereof are still within the scope of the present invention, which is intended to be defined and limited by the appended claims.

What is claimed:

1. An electrode system (ES) for measuring an electrical parameter of a sample, comprising:
   (a) a frame;
   (b) a first electrode coupled to the frame;
   (c) a slider movably coupled to the frame;
   (d) a second electrode movable relative to said first electrode and coupled to the slider;
   (e) force means disposed between the slider and frame for applying a force to said slider; and
   (f) adjusting means for passively adjusting said force means so as to maintain a pressure on the sample substantially uniform, whether the ES is horizontally or vertically oriented.

2. Electrode system of claim 1 wherein said force means comprises spring means providing an expansive force, and further comprising means for adjusting the parallelism of said electrodes.

3. Electrode system of claim 1 further comprising:
   (g) micrometer means, coupled to the frame and slider, for moving the slider.

4. Electrode system of claim 1 wherein the first and second electrodes are parallel to one another.

5. Electrode system of claim 1 wherein the first electrode is coupled to the frame with at least three set screws and second spring means; wherein the set screws are engaged with the frame and disposed to push the first electrode away from the frame, and the second spring means are disposed to pull the first electrode to the frame.

6. Electrode system of any one of the preceding claims wherein the first and second electrodes are adapted for four terminal pair measurements.

7. Electrode system of claim 1 wherein the second electrode comprises a main electrode and a guard electrode insulated from the main electrode.

8. An electrode system (ES) for measuring an electrical parameter of a sample, comprising:
   (a) a frame;
   (b) a first electrode coupled to the frame;
   (c) a slider movably coupled to the frame;
   (d) a second electrode movable relative to said first electrode and coupled to the slider;
   (e) force means disposed between the slider and frame for applying a force to said slider;
   (f) adjusting means for passively adjusting said force means so as to maintain a pressure on the sample substantially uniform, whether the ES is horizontally or vertically oriented; and
   (g) micrometer means, coupled to the frame and slider, for moving the slider;
wherein the sample is disposed between the first and second electrodes.

9. Electrode system of claim 8 wherein the first and second electrodes are parallel to one another.

10. Electrode system of claim 8 wherein the first electrode is coupled to the frame with at least three set screws and second spring means; wherein the set screws are engaged with the frame and disposed to push the first electrode away from the frame, and the second spring means are disposed to pull the first electrode to the frame.

11. Electrode system of any one of claims 8, 9, or 10 wherein the first and second electrodes are adapted for four terminal air measurements.

12. Electrode system of claim 8 wherein the second electrode comprises a main electrode and a guard electrode insulated from the main electrode.

13. Electrode system of claim 8 wherein said force means comprises spring means providing an expansive force.

14. An electrode system for measuring an electrical parameter of a sample while the ES is horizontally or vertically oriented, comprising:
   (a) a frame;
   (b) a first electrode coupled to the frame;
   (c) a slider movably coupled to the frame;
   (d) a second movable electrode coupled to the slider;
   (e) first spring means disposed between the slider and frame for providing an expansive force, the force dependent upon whether the ES is horizontally or vertically oriented;
   (f) micrometer means, coupled to the frame and slider, for moving the slider; and
   (g) a sample disposed between the first and second electrodes;
wherein the first electrode is coupled to the frame with at least three set screws and second spring means, the set screws being engaged with the frame and disposed to push the first electrode away from the frame, and the second spring means being disposed to pull the first electrode to the frame.

15. A method of operating an electrode system comprising (a) a frame; (b) a first electrode coupled to the frame; (c) slider movably coupled to the frame; and (d) a second electrode movable relative to said first electrode and coupled to the slider, said method comprising the following steps:
   (a) inserting a sample between said first electrode and said second electrode;
   (b) applying a force for moving said first electrode toward said second electrode; and
   (c) passively adjusting said force so as to maintain a pressure on the sample substantially uniform, whether the ES is horizontally or vertically oriented.

16. A method of calibrating an electrode system comprising two substantially parallel plate electrodes, first adjusting means for adjusting the distance D between the respective centers of the two electrodes, and second adjusting means for adjusting the parallelism A of the two electrodes; the method comprising the steps of:
   (a) coupling a capacitance measuring instrument to the electrode system so that the capacitance measuring instrument will be capable of measuring the capacitance between the parallel plate electrodes;
   (b) adjusting the distance D to a given, non-zero value;
   (c) measuring the capacitance between the parallel plate electrodes;
   (d) adjusting the parallelism A of the two parallel plate electrodes until the measured capacitance falls within a tolerable calculated range of capacitances corresponding to the distance D and a maximum tolerable value of A.

* * * * *